US00PP33566P2

(12) United States Plant Patent
Trees

(10) Patent No.: US PP33,566 P2
(45) Date of Patent: Oct. 19, 2021

(54) ***BUDDLEIA* PLANT NAMED 'DAPCONWHI'**

(50) Latin Name: *Buddleia davidii*
Varietal Denomination: Dapconwhi

(71) Applicant: THE CONARD PYLE COMPANY, West Grove, PA (US)

(72) Inventor: Scott C. Trees, Arroyo Grande, CA (US)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 17/130,800

(22) Filed: Dec. 22, 2020

(51) Int. Cl.
*A01H 5/02* (2018.01)
*A01H 6/00* (2018.01)

(52) U.S. Cl.
USPC ..... Plt./242

(58) Field of Classification Search
USPC ..... Plt./242
CPC ..... A01H 6/00; A01H 5/02
See application file for complete search history.

(56) References Cited

U.S. PATENT DOCUMENTS

PP28,795 P3 12/2017 Wood

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of *Buddleia* plant, referred to by its cultivar name, 'Dapconwhi', is disclosed. The new variety forms attractive white colored flowers. Attractive, medium green colored foliage is formed. The growth habit is compact, mounded and the plant has moderate growth vigor. The new variety is well suited for providing attractive ornamentation in the landscape.

1 Drawing Sheet

Botanical/commercial classification:
Latin name: *Buddleia davidii.*
Varietal denomination: 'Dapconwhi'.

SUMMARY OF THE INVENTION

The new variety of *Buddleia davidii* plant originated in a controlled breeding program in Guadalupe, Calif. during June 2015. The objective of the breeding program was the development of a series of *Buddleia* cultivars with compact and well-branched habits. The new cultivar was created by self-pollination wherein seed and pollen from a single variety were used in the hope that they would contribute the desired characteristics to progeny of the self-pollination. The parent, which was both the female parent (i.e., the seed parent) and the male parent (i.e, the pollen parent) was an unnamed breeder seedling variety (not patented). The parent unnamed breeder seedling variety was created by crossing two other/different unnamed breeder seedlings varieties (neither patented).

The parentage of the new variety can be summarized as follows:

unnamed breeder seedling x unnamed breeder seedling

The new cultivar was discovered and selected as a single flowering plant from the progeny resulting from the above stated self-pollination during July 2016 in a controlled environment in Guadalupe, Calif. Selective study resulted in the identification of a single plant of the new variety.

It was found that the new variety of *Buddleia* plant of the present invention:

(a) forms white colored flowers,
(b) displays medium green colored foliage, and (c) exhibits a moderately vigorous and compact, mounded growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the unnamed breeder seedling parental variety displays lavender blue colored flowers and compact to upright growth habit, while the new variety provides white colored flowers and a compact, mounded growth habit. Moreover, the new variety can also be distinguished from other similar varieties that are commercially available. For instance, the new variety of the present invention can readily be distinguished from the 'SMNBDW' variety (U.S. Plant Pat. No. 28,795), as the new cultivar displays sturdier stems and denser growth habit with new blooms that hid the old blooms as compared to the plants of the 'SMNBDW' variety.

The new variety has been found to undergo asexual propagation by terminal stem cuttings. Asexual propagation by terminal stem cuttings in Guadalupe, Calif. since August 2016 has shown that the characteristics of the new variety are stable and are strictly transmissible by such asexual propagation from one generation to another. Accordingly, the new variety undergoes asexual propagation in a true-to-type manner.

The new variety has been named 'Dapconwhi'.

The new variety was first offered for sale on Jan. 8, 2020 at Baltimore, Md. by the inventor or by another who obtained the new variety directly or indirectly from the inventor.

BRIEF DESCRIPTION OF THE PHOTOGRAPH

The accompanying photograph shows as nearly true as it is reasonably possible to make the same, in a color illustration of this character, typical specimens of the plant and plant parts of the new variety. Colors in the photograph may differ slightly from the color values cited in the detailed description, which accurately describes the colors of the 'Dapconwhi' variety. The plant was grown in one-gallon pots for approximately four months outside at Cochranville, Pa. The plant was pinched once after transplant.

Drawing—illustrates a specimen of the plant displaying the overall growth and flowering habit—side view.

DETAILED BOTANICAL DESCRIPTION

The chart used in the identification of the colors is that of The Royal Horticultural Society (R.H.S. Color Chart), 2015 edition, London, England. The terminology which precedes reference to the chart has been added to indicate the corresponding color in more common terms. The color values were determined in August 2020 under natural light conditions in Cochranville, Pa. The description is based on the observation of plants produced from cuttings from stock plants and grown in one-gallon containers for approximately four months in an outdoor nursery in Cochranville, Pa. Plants were pinched once after transplant.

Class: *Buddleia* Plant.

Common name: Butterfly bush.

Propagation:

*Type cutting*.—Terminal stem.

*Time to initiate roots*.—Approximately 10 to 14 days on average.

*Time to produce a rooted cutting*.—Approximately 21 to 25 days on average.

*Root description*.—Fibrous.

*Rooting habit*.—Freely branching.

Plant:

*Habit*.—Moderate growth vigor and compact, mounding growth habit.

*Commercial crop time*.—Approximately 2 months from a rooted cutting to finish in a 1-gallon container on average.

*Size*.—Approximately 25.0 cm in height from soil level to top of plant plane on average; and approximately 35.0 cm in width on average.

Branches:

*Branching habit*.—Freely branching, pinching enhances basal branching.

*Quantity of main branches per plant*.—Approximately 5 on average.

*Strength*.—Commonly strong, somewhat flexible and becomes woody with age.

*Size*.—Length: approximately 15,0 cm on average. — diameter: approximately 4.0 mm on average. — length of central internode: approximately 2.0 cm on average.

*Texture*.—Viscid, densely glandular pubescent.

*Color*.—Young stems: commonly near Yellow-Green Group 146C with some pubescence color of near Greyed-Green Group 192C. — mature stems: commonly near Greyed-Orange Group 177C.

Foliage:

*Number of leaves*.—Approximately 30 to 40 per branch on average; and approximately 8 per branched lateral stem on average.

*Fragrance*.—None detected.

*Form*.—Simple.

*Arrangement*.—Opposite.

*Durability to stress*.—Moderate to high.

Leaves:

*Aspect*.—Primarily perpendicular to stem.

*Shape*.—General: lanceolate to oblanceolate. — margin: entire to serrulate. — apex: acute. — base: attenuate.

*Venation*.—Pattern: pinnate, reticulate. — upper surface color: indistinguishable from the upper surface leaf color. — under surface color: commonly near Greyed- Green Group 191B.

*Size*.—Length of mature leaf: approximately 6.2 cm on average. — width of mature leaf: approximately 1.5 cm on average.

*Texture*.—Upper and lower surfaces: pubescent.

*Color*.—Upper surface of mature foliage: commonly near Green Group 137A. — lower surface of mature foliage: commonly near Greyed-Green Group 194A.

*Petiole*.—Shape: rounded, slightly curved. — length: approximately 1.0 mm on average. — width: approximately 1.0 mm on average. — texture: moderately pubescent with lanulose hairs. — color: commonly near Yellow-Green Group 145A.

Inflorescence:

*Quantity*.—Approximately 40 open inflorescences per plant on average, and approximately 132 flowers per inflorescence open at a time, opening from base to apex.

*Type*.—Terminal panicles, each panicle having about 2 to 4 branches on average; and flowers persistent, facing upward and outward.

*Fragrance*.—Moderately strong sweet scent.

*Depth or height*.—Approximately 5.0 cm on average.

*Width*.—Approximately 3.5 cm on average.

*Rachis*.—Strength: strong. — length: approximately 5.0 cm on average at the time flowers begin to open and approximately 7.0 cm at the end of flowering. — diameter: approximately 2.0 mm on average. — texture: pubescent with stellate hairs. — color: commonly near Greyed-Green Group 193C.

Flower:

*Type*.—Single, salverform.

*Bud just before opening*.—Shape: oblong. — length: approximately 5.0 mm on average. — diameter: approximately 1.0 mm on average. — texture: glabrous. — color of petals: commonly near White Group NN155C.

*Corolla*.—Shape: rotate, commonly 4 petals arranged in a single whorl. — depth: approximately 8.0 mm on average. — width: approximately 7.0 mm on average.

*Petals*.—Shape: rotund. — margin: erosulate. — apex: rounded. — length from throat: approximately 3.0 mm on average. — width: approximately 3.0 mm on average. — texture of upper and lower surfaces: glabrous. color of upper and lower surfaces when first and fully open: commonly near White Group NN155C.

*Corolla tube*.—Length: approximately 7.0 mm on average. — width: approximately 1.0 mm on average. — diameter of throat opening: approximately 1.0 mm on average. — inner surface: texture is glabrous and color is commonly near Orange Group N25C. — outer surface: texture is glabrous and color is commonly near Orange Group 26B.

*Calyx*.—Shape: tubular. — length: approximately 3.0 mm on average. — diameter: approximately 1.0 mm on average.

*Sepals*.—Quantity per flower: commonly 4 on average, fused at base. — length of free portion: approximately 1.0 mm on average. — width: commonly less than 1.0 mm. — apex: acute. — margin of free portion: entire. — inner surface: — texture: moderately pubescent. — color: commonly near Yellow-Green Group 144A. — outer surface: — texture: densely pubescent. — color: commonly near Yellow-Green Group 144A.

*Reproductive organs*.—Androecium: — Stamen: commonly 4 per flower, completely adnate to corolla. — anther: shape is lanceolate, length is approximately 1.0 mm on average, and color is commonly near Greyed-Orange Group N167C. pollen: amount is moderate and coloration is commonly near Greyed-Orange Group 168D. — gynoecium: — pistil: commonly 1 per flower, length is approximately 2.0 mm on average. — stigma: shape is cleft, two-parted, length is approximately 1.0 mm on average. — seed and fruit: none have been observed to date.

Development:

*Blooming*.—Freely flowering under outdoor growing conditions with substantially continuous blooming from late spring through mid-fall.

*Lastingness of individual flower*.—Approximately 5 days on average.

*Tolerance to disease and pest*.—Not observed to date.

The new 'DAPCONWHI' variety has not been observed under all possible environmental conditions to date. Accordingly, it is possible that the phenotypic expression may vary somewhat with changes in light intensity and duration, cultural practices, and other environmental conditions.

I claim:

1. A new and distinct cultivar of *Buddleia* plant named 'DAPCONWHI' characterized by the following combination of characteristics:

(a) forms white colored flowers, (b) displays medium green colored foliage, and (c) exhibits a moderately vigorous and compact, mounded growth habit;

substantially as herein shown and described.

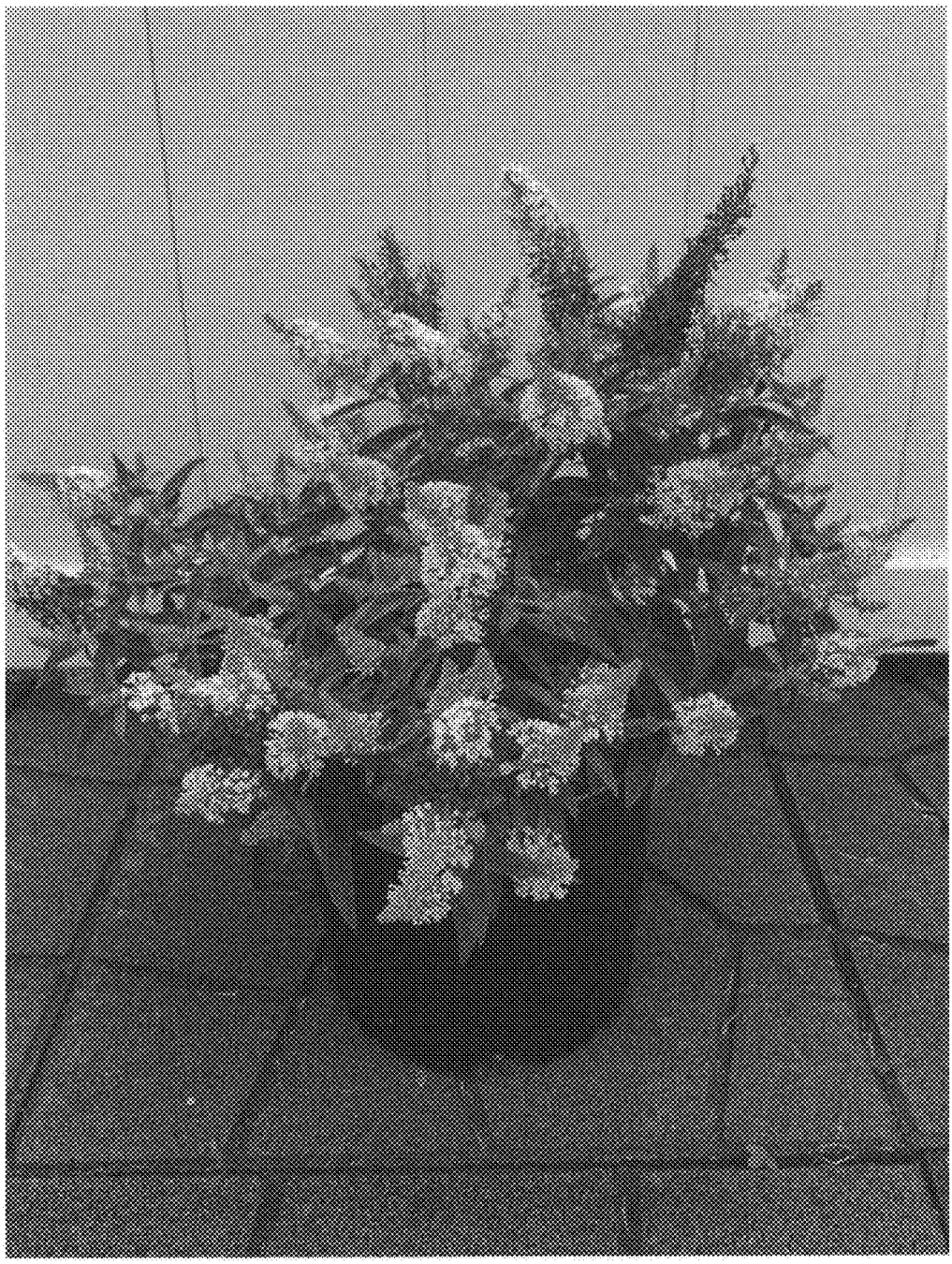

* * * * *